United States Patent [19]

Suzuki et al.

[11] Patent Number: 5,677,940
[45] Date of Patent: Oct. 14, 1997

[54] DIGITAL X-RAY IMAGING APPARATUS

[75] Inventors: Masakazu Suzuki; Keisuke Mori; Akifumi Tachibana; Kazunari Matoba, all of Kyoto; Koei Yamamoto; Seiichiro Mizuno, both of Hamamatsu, all of Japan

[73] Assignees: J. Morita Manufacturing Corporation, Kyoto; Hamamatsu Photonics Kabushiki Kaisha, Shizuoka, both of Japan

[21] Appl. No.: 618,991

[22] Filed: Mar. 20, 1996

[30] Foreign Application Priority Data

Mar. 24, 1995 [JP] Japan ................................. 7-066602

[51] Int. Cl.$^6$ ........................................................ A61B 6/14
[52] U.S. Cl. ............................ 378/38; 378/40; 378/98.8; 250/370.4; 250/370.9
[58] Field of Search ............................... 378/38, 39, 40, 378/98.8; 250/370.4, 370.09

[56] References Cited

U.S. PATENT DOCUMENTS 5,440,130  8/1995  Cox et al. ...................... 250/370.09
5,461,233 10/1995  Yamamoto et al. .................. 378/40
5,528,043  6/1996  Spivey et al. ................... 250/370.09

FOREIGN PATENT DOCUMENTS 61-22841  1/1986  Japan.
4-48169  11/1992  Japan.

Primary Examiner—Don Wong
Attorney, Agent, or Firm—Koda and Androlia

[57] ABSTRACT

A digital X-ray imaging apparatus comprises an X-ray generator 6 for generating X-rays toward a subject, an X-ray imaging device 7 for detecting an image of X-rays having passed through the subject, a swivel member 4 and a horizontal movement means 8 provided with the X-ray generator 6 and the X-ray imaging device 7 opposed to each other to relatively move the X-ray generator 6 and the X-ray imaging device 7 with respect to the subject, a CPU 21 for producing a tomographic image in accordance with an imaging signal from the X-ray imaging device 7, frame memories and an image display unit 26 for displaying the tomographic image. The X-ray imaging device 7 includes a MOS image sensor having a plurality of two-dimensional light-receiving pixels. With this configuration, a tomographic image along a given tomographic plane can be produced by a signal X-ray imaging operation, and the imaging sensitivity of the digital X-ray imaging apparatus can be enhanced.

6 Claims, 12 Drawing Sheets

| J1 | | | J2 | | | J1+J2 | |
|---|---|---|---|---|---|---|---|
| C c | | + | E d | | = | C c | E d |
| B b | | | D c | | | B b | D c |
| A a | | | C b | | | A a | C b |

| J1 | | | J1s | |
|---|---|---|---|---|
| C c | | ⇒ | D d | |
| B b | | | C c | |
| A a | | | B b | |

| J1s | | | J2 | | | J1s+J2 | |
|---|---|---|---|---|---|---|---|
| D d | | + | E d | | = | D d | E d |
| C c | | | D c | | | C c | D c |
| B b | | | C b | | | B b | C b |

DIGITAL X-RAY IMAGING APPARATUS

BACKGROUND OF THE INVENTION

1. Field of the Invention

The present invention relates to a digital X-ray imaging apparatus for performing panoramic or linear tomographic imaging along desired tomographic planes of subjects, such as the head, body, and hands and legs of the human body.

2. Description of the Related Art

As related art, Japanese Laid-open Patent Application No. Sho 61-22841 and Japanese Utility Model Publication No. Hei 4-48169 disclose X-ray imaging apparatuses for performing TDI (Time Delay Integration) of an image signal by changing the frequency of a charge transfer clock in accordance with the movement of an X-ray image formed on a CCD sensor while the image is moved.

However, since the TDI operation is performed by using a CCD sensor in the apparatuses disclosed in Japanese Laid-open Patent Application No. Sho 61-22841 and Japanese Utility Model Publication No. Hei 4-48169, an image signal only for a specific tomographic plane is obtained. Therefore, when it is desirable to see a different tomographic image, X-ray imaging must be performed again. It is thus inevitable that radiation dosage increases.

SUMMARY OF THE INVENTION

The object of the present invention is to provide a digital X-ray imaging apparatus capable of taking tomographic images along a given tomographic plane by a single X-ray imaging operation and also capable of performing highly sensitive panoramic or linear tomographic imaging.

The invention relates to a digital X-ray imaging apparatus comprising:

an X-ray generator for emitting X-rays toward a subject, an X-ray imaging device for detecting an image of X-rays having passed through the subject;

means for moving the X-ray generator and the X-ray imaging device that are opposed to each other relative to the subject;

means for signal processing to produce a tomographic image in accordance with an imaging signal from the X-ray imaging device; and means for displaying a tomographic image produced by the signal processing means, wherein the X-ray imaging device includes a MOS sensor having a plurality of light-receiving pixels arranged in two dimensions.

According to the invention, a MOS (metal-oxide semiconductor) sensor having a plurality light-receiving pixels arranged in two dimensions is used to attain highly sensitive imaging. The sensitivity of the MOS sensor is approximately 1.75 times as high as that of a conventional CCD sensor, for example, in terms of quantum efficiency. Even if a reduction in the efficiency to 80% because of the opening ratio of the light-receiving pixels is allowed for, the sensitivity can be improved approximately 1.4 times as a whole.

Furthermore, after an X-ray image of the subject is taken while the X-ray generator and the X-ray imaging device are moved with respect to the subject at a predetermined resolution, a tomographic image along a given tomographic plane can be produced by the signal processing means. Therefore, a great number of tomographic images can be reproduced from the image data obtained by a single X-ray imaging operation.

Furthermore, the X-ray imaging device of the invention comprises:

a plurality of MOS sensors connected in multistages;

a pixel selection circuit for selecting reading pixels for each MOS sensor; and a plurality of shift registers for receiving an image signal from each light-receiving pixel disposed and selected for each MOS sensor and for transferring the image signal on the basis of time series.

Furthermore, according to the invention, a plurality of MOS sensors are connected in multistages, and data is transferred in parallel from a plurality of shift registers disposed for each MOS sensor, whereby the data transfer speed is improved greatly as a whole. Even when a MOS sensor having a large area cannot be obtained because of production yield, a large light-receiving area can be attained by connecting a plurality of MOS sensors in multistages.

Furthermore, the apparatus of the invention comprises means for selecting a panoramic or linear tomographic imaging mode;

wherein the range of pixels to be read by the MOS sensor is selected in accordance with the selected imaging mode.

Furthermore, according to the invention, a single MOS sensor can be used in both the panoramic and linear imaging modes by selectively changing the range of pixels to be read by the MOS sensor in accordance with the selected panoramic or linear imaging mode.

Furthermore, the apparatus of the invention comprises:

a first slit plate for limiting the X-ray irradiation field of the subject; and a second slit plate for limiting the X-ray incoming region of the X-ray imaging device, wherein the opening ranges of the first and second slit plates are selectively changed in accordance with the imaging mode selected by the imaging mode selection means.

Furthermore, according to the invention, imaging conditions can be set easily by selectively changing the opening ranges of the first and second slit plates in accordance with the imaging mode.

Furthermore, the invention is characterized in that the opening width of the second slit plate is adjusted during imaging in the panoramic tomographic imaging mode.

Furthermore, according to the invention, since a tomographic width can be controlled by changing the opening width of the second slit plate in accordance with an imaging region in the panoramic tomographic imaging mode, an easy-to-diagnose panoramic image can be obtained with few unnecessary tomographic images.

As described above, it is possible to attain high-sensitivity tomographic imaging and to produce a tomographic image along a given tomographic plane after imaging is completed. Consequently, the number of X-ray imaging operations can be reduced, whereby radiation dosage can be decreased significantly.

Furthermore, by the multistage connection of the MOS sensors, the imaging area can be made larger easily, and the data transfer speed can be improved greatly as a whole.

Furthermore, optimal imaging conditions can be set quickly and securely in accordance with the selection of the panoramic or linear tomographic imaging mode, whereby a high-quality tomographic image can be obtained in accordance with the selected imaging mode.

BRIEF DESCRIPTION OF THE DRAWINGS

Other and further objects, features, and advantages of the invention will be more explicit from the following detailed description taken with reference to the drawings wherein:

FIG. 12 is an explanatory view showing panoramic tomographic imaging;

FIG. 13 is a structural view showing an embodiment of a first slit plate 6b and a second slit plate 7a;

FIG. 14 is a structural view showing another embodiment of the first slit plate 6b and the second slit plate 7a;

FIG. 15 is a structural view showing still another embodiment of the first slit plate 6b and the second slit plate 7a.

DETAILED DESCRIPTION OF THE PREFERRED EMBODIMENTS

With reference to the accompanying drawings preferred embodiments of the invention will be explained in details.

Figure 1:
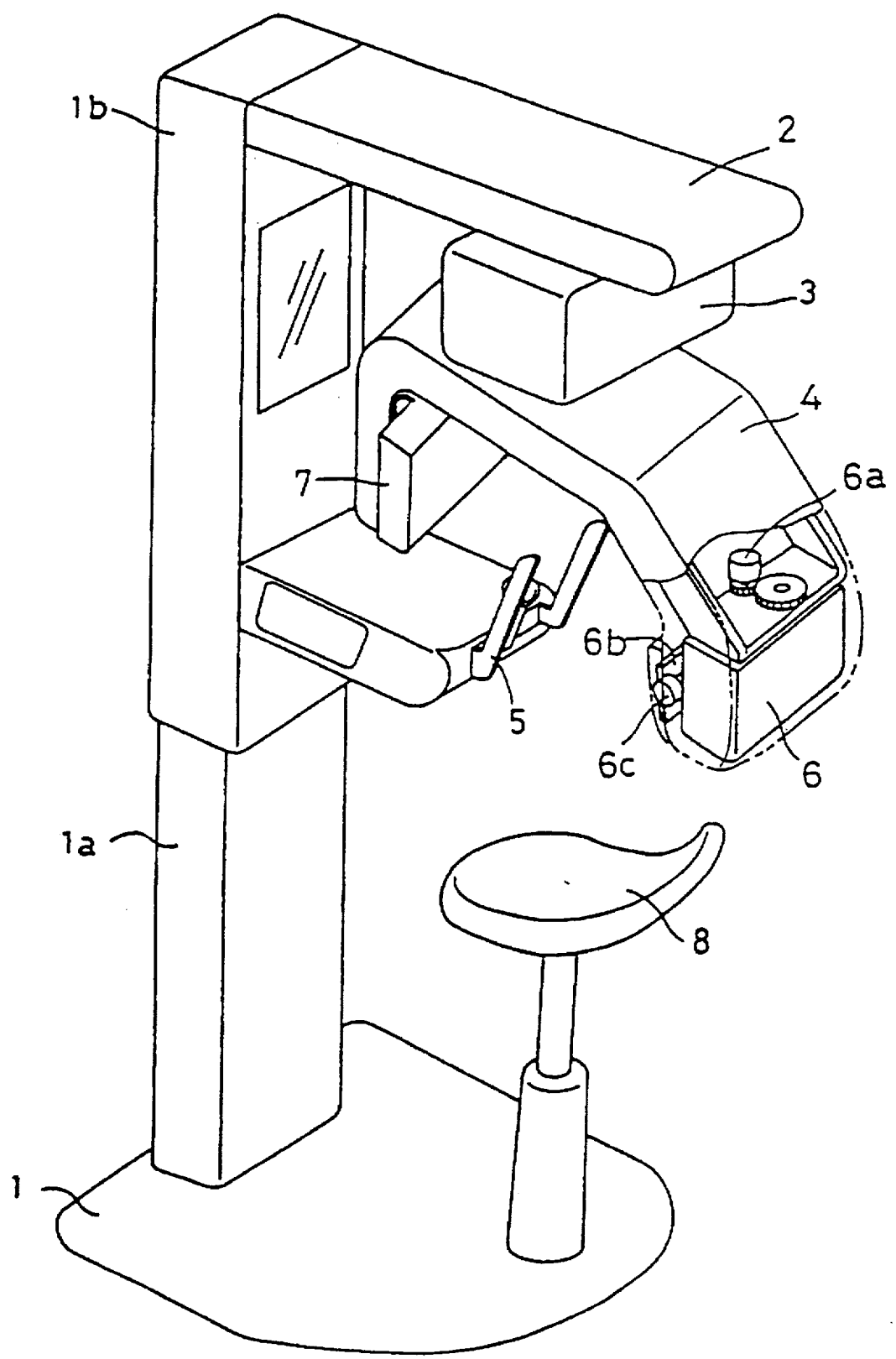
FIG. 1 is an overall perspective view of an embodiment of the invention.

FIG. 1 is an overall perspective view of an embodiment of the invention. A chair 8 for a patient and a column 1a are provided on a base 1. An elevating frame 1b is provided on the column 1a so as to ascend and descend along the column 1a. The elevating frame 1b is provided with a positioning member 5 for positioning the head of the patient. A horizontal arm 2 is extended from the upper end of the elevating frame 1b. A horizontal movement mechanism 3 incorporating an X-Y table and a rotation table is installed in the vicinity of the tip of the horizontal arm 2. A swivel member 4 (such as a rotary arm) is installed at the moving portion of the horizontal movement mechanism 3 so as to be able to rotate around a given position on a horizontal plane. An X-ray source 6 is provided at one end of the swivel member 4, and an X-ray imaging device 7 is provided at the other end. The X-ray source 6 can swing at a desired angle by a rotation motor 6a. Furthermore, a first slit plate 6b for limiting the X-ray irradiation field is provided in front of the X-ray source 6, and a drive motor 6c is installed so as to adjust the opening range of the first slit plate 6b.

Figure 2:
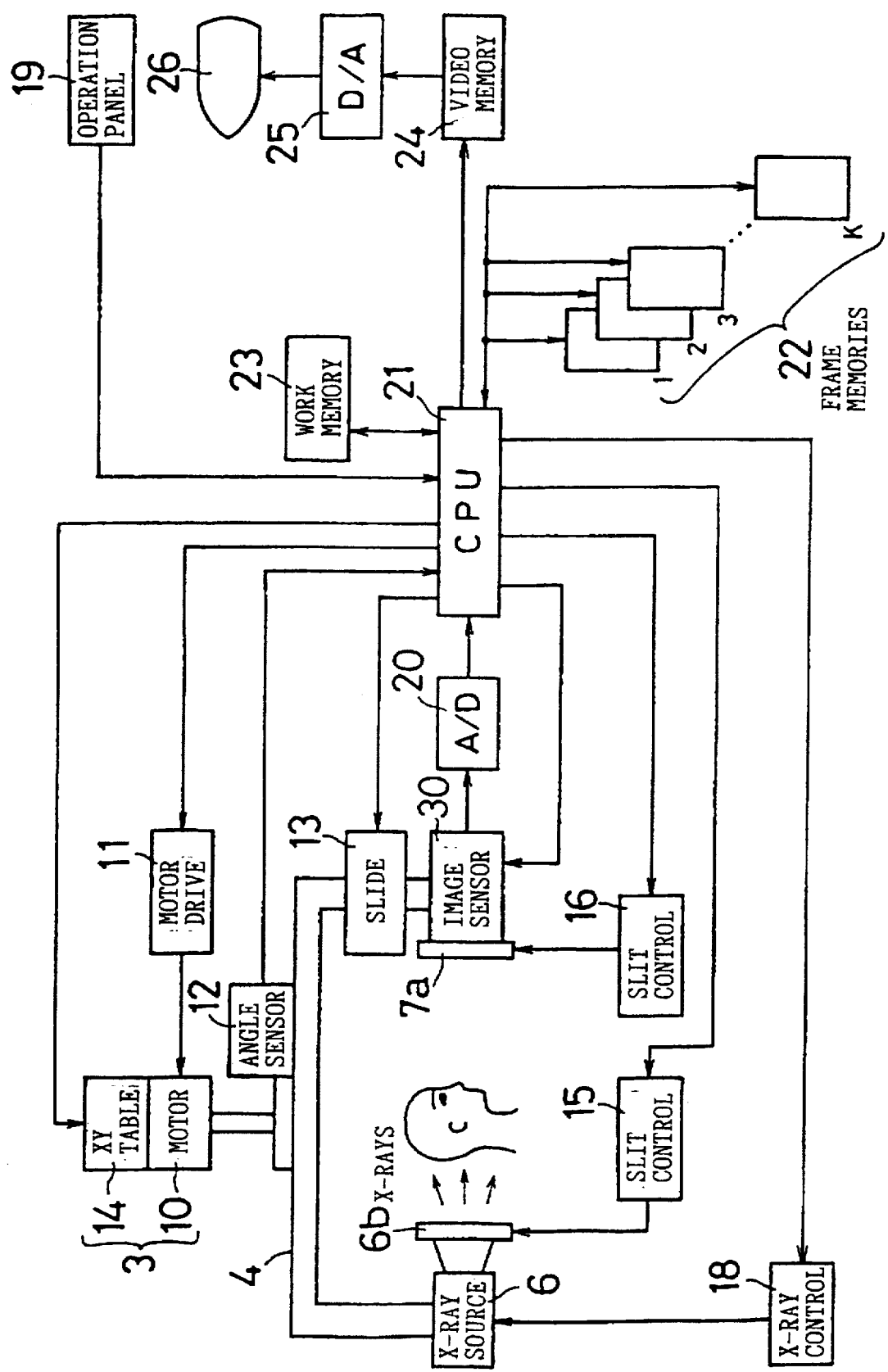
FIG. 2 is an overall configuration view of an embodiment of the invention.

FIG. 2 is an overall configuration view of an embodiment of the invention. The X-ray source 6 emits X-rays toward the subject, and the X-ray irradiation field is controlled by the first slit plate 6b. An X-ray tube (not shown) is included in the X-ray source 6. The X-ray irradiation dosage to the patient is controlled by adjusting imaging conditions, such as tube current, tube voltage, power application time, etc.

The X-ray imaging device 7 includes a MOS image sensor having a plurality of light-receiving pixels arranged in two dimension to detect an image of X-rays having passed through the object. A second slit plate 7a for limiting the X-ray incoming region is provided in front of the X-ray imaging device 7.

The back surface of the MOS image sensor 30 and the interior of the X-ray imaging device 7 incorporating the MOS image sensor 30 are shielded against X-rays to prevent adverse effects due to the dissipation of X-rays.

The swivel member 4 holds the X-ray source 6 and the X-ray imaging device 7 opposingly to each other and rotates around the subject in the panoramic tomographic imaging mode. Furthermore, in the linear tomographic imaging mode, a slide mechanism 13 is provided so as to linearly move the X-ray imaging device 7 with respect to the subject. The swivel member 4 is driven by a motor 10 constituting the rotation table, and the rotation angle of the swivel member 4 is detected by an angle sensor 12. The motor 10 is mounted on the moving portion of an XY table 14, and its rotation center is adjusted as desired on a horizontal plane.

An image signal outputted from the X-ray imaging device 7 is converted into 10-bit (=1024 levels) digital data, for example, by an AD converter 20, taken in a CPU (central processing unit) 21, and then stored in frame memories 22. A tomographic image taken along a given tomographic plane can be reproduced from the image data stored in the frame memories 22 by a predetermined arithmetic operation process. The reproduced tomographic image is delivered to a video memory 24, converted into an analog signal by a DA converter 25, and then displayed by an image display unit 26, such as a CRT (cathode-ray tube) display, so as to be made available for a variety of diagnoses.

A work memory 23 required for signal processing is connected to the CPU 21, and an operation panel 19 incorporating a panel switch, an X-ray irradiation switch, etc. is also connected to the CPU 21. Furthermore, the CPU 21 is connected to a motor drive circuit 11 for driving the arm motor 10, slit control circuits 15, 16 for controlling the opening ranges of the first slit plate 6b and the second slit plate 7a, respectively. In addition, the CPU 21 delivers a clock signal for driving the MOS image sensors of the X-ray imaging device 7.

An X-ray control circuit 18 can feedback-control an X-ray irradiation dosage to the subject in accordance with the signal taken by the MOS image sensor of the X-ray imaging device 7.

Figure 3A:
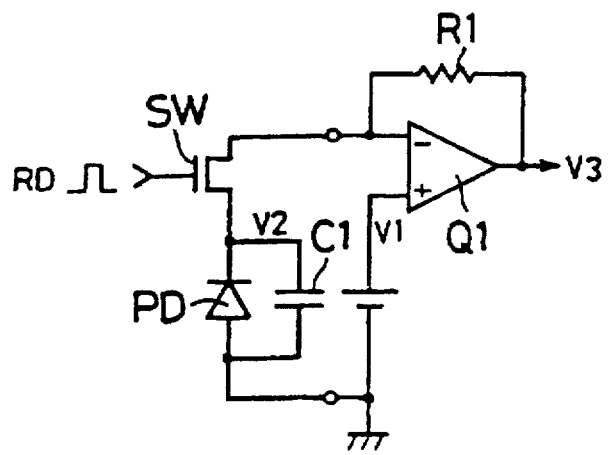
FIG. 3A is a circuit diagram showing the operation principle of a MOS image sensor.
Figure 3B:
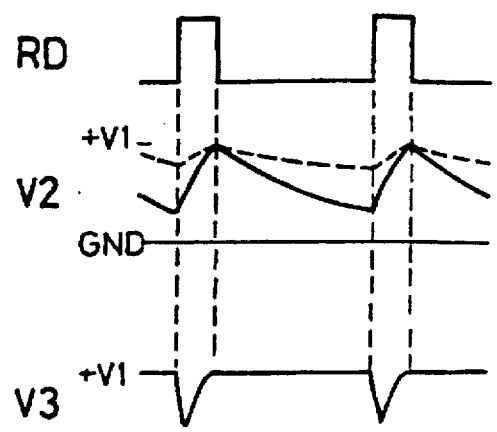
FIG. 3B is a timing chart of the operation of the sensor.

FIG. 3a is a circuit diagram showing the operation principle of the MOS image sensor, and FIG. 3b is a timing chart of the operation of the sensor. A photodiode PD constituting a light-receiving pixel converts incoming light into an electrical signal. The photodiode PD is connected to a switch SW comprising a MOSFET in series, and the switch SW is further connected to the inverting input terminal of an operational amplifier Q1. A feedback resistor R1 is connected to the operational amplifier Q1 to form a current-voltage conversion circuit, whereby input current is outputted as a voltage signal. Voltage V1 is applied between the noninverting input terminal of the operational amplifier Q1 and the ground (GND).

In FIG. 3b, when a positive reading pulse RD enters the gate of the switch SW, the switch SW opens and the photodiode PD is reverse-biased and a junction capacitor C1 is charged with a certain amount of charges. Next, when the switch SW closes and light enters during the accumulation of charges, the accumulated charges are discharged by the charges due to the incoming light, and the potential at the cathode of the photodiode PD becomes close to the ground potential- The amount of charges to be discharged increases in proportion to the amount of the incoming light. Next, when the reading pulse RD enters the gate of the switch SW, and the switch SW opens, the amount of charges corresponding to the charges discharged during the accumulation period is supplied via the feedback resistor R1, and the photodiode PD is reverse-biased again and initialized. At this time, a potential difference is generated between both ends of the feedback resistor R1 because of the charge current, and outputted as a voltage signal from the operational amplifier Q1. Since this charge current corresponds to the discharge current due to the incoming light, the amount of the incoming light is detected by measuring the output voltage.

Figure 3C:
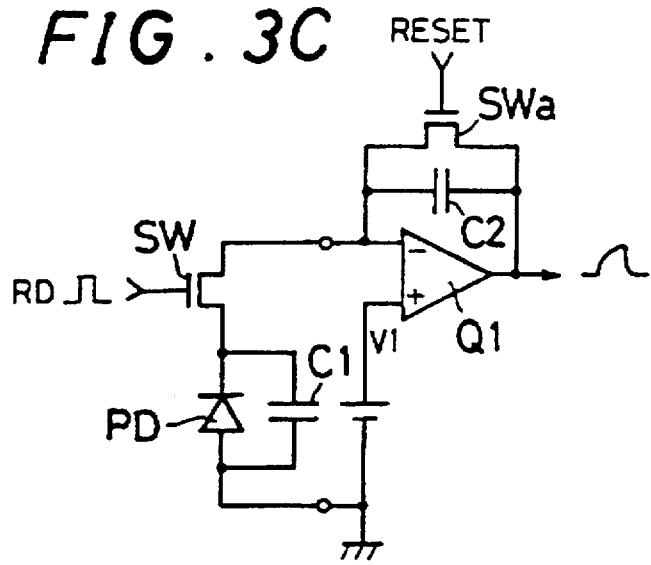
FIG. 3C is a circuit diagram of another embodiment of the circuit.

FIG. 3c shows another embodiment of the signal reading circuit. In this circuit, an integration capacitor C2 and a switch SWa are connected between the inverting input terminal and the output terminal of an operational amplifier Q1, thereby forming a current integration circuit as a whole. Immediately before a reading switch SW opens, the integration capacitor C2 of the integration circuit is discharged by an external reset pulse. Next, when the switch SW opens, a junction capacitor C1 of a photodiode PD is charged from the power source with the charges corresponding to the light output during the accumulation period, the potential of the photodiode PD is initialized to a positive voltage of V1, and the integration capacitor C2 is also charged by the charging current. Consequently, a square integration waveform is obtained at the output terminal of the integration circuit. Therefore, any special circuits, such as a sample-and-hold circuit, are not necessary, and the signal processing at a later stage can be made easier.

Figure 4:
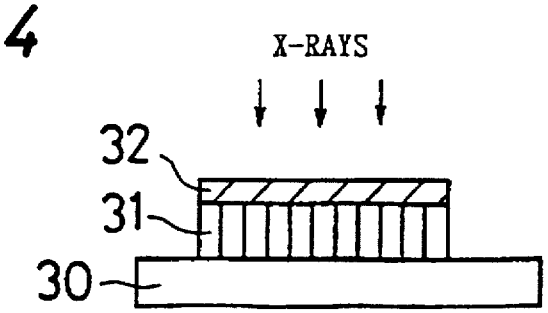
FIG. 4 is a sectional view showing the structure of an X-ray image sensor.

FIG. 4 is a sectional view showing the structure of the X-ray image sensor. A fiber-optic element (FOP) 31 for transferring an optical image is provided on the MOS image sensor 30 comprising two-dimensional photodiodes PD constituting light-receiving pixels. Furthermore, a scintillator layer 32 for converting X-rays into visible light is formed on the fiber-optic element 31. An image of X-rays having passed through the subject is converted into a visible light image by the scintillator layer 32, transferred by the fiber-optic element 31 and directly subjected to photoelectric conversion by the MOS image sensor 30.

Figure 5:
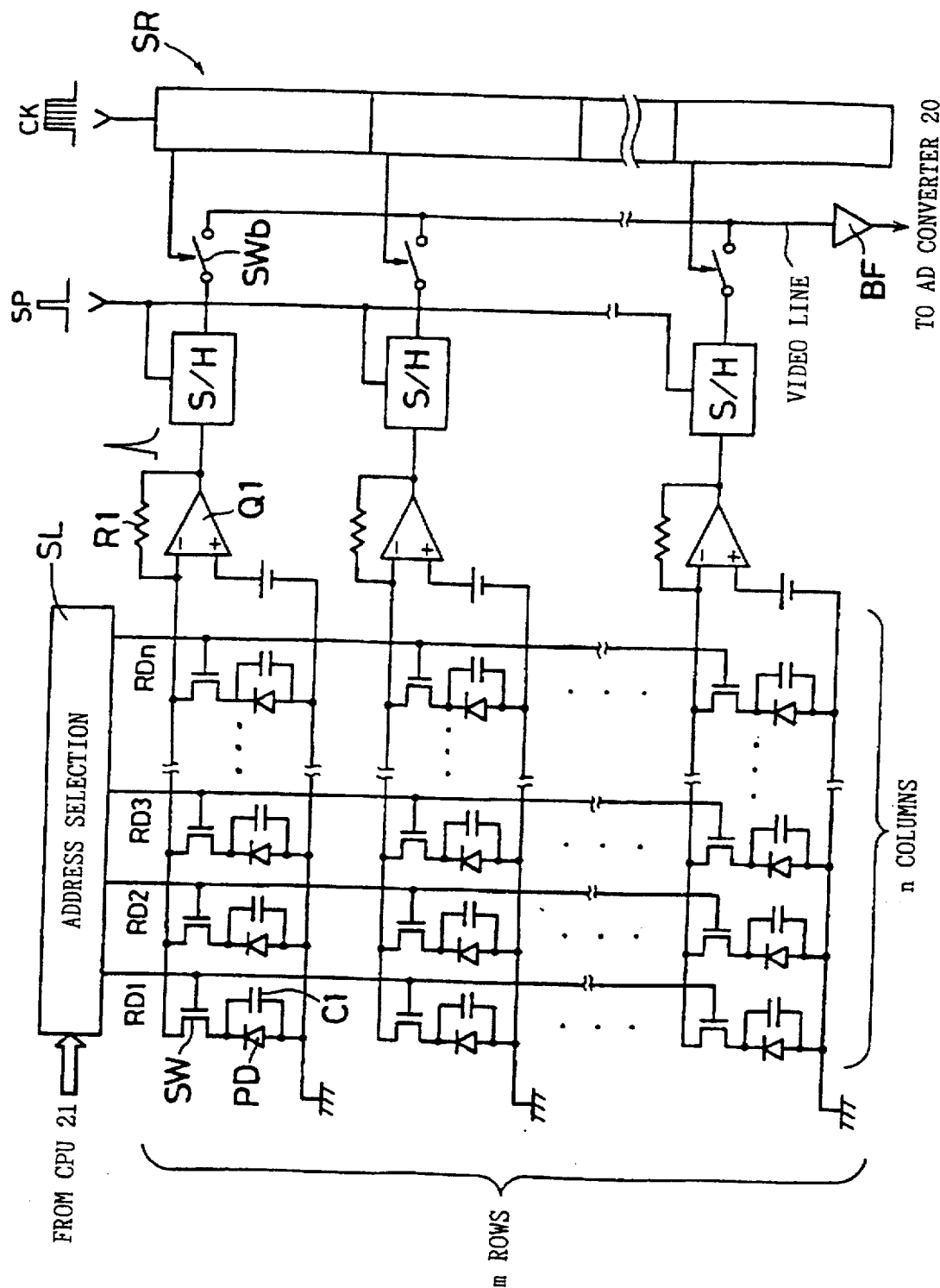
FIG. 5 shows a drive circuit for a MOS image sensor

FIG. 5 shows a drive circuit for the MOS image sensor 30. Photodiodes PD used as light-receiving pixels are arranged in a matrix of m rows×n columns. A junction capacitor C1 is connected in parallel with each photodiode PD, and a reading switch SW is connected in series with each photodiode PD. An address selection circuit SL is connected to the gages of the switches SW so as to select photodiodes PD to be read in accordance with a signal from the CPU 21.

The output sides of the switches SW in each row are connected in common and supplied to an operational amplifier Q1 constituting a current-voltage conversion circuit. The output of the operational amplifier Q1 is sampled by a sample-and-hold (S/H) circuit. Each sample-and-hold circuit is connected to a switch SWb, which is opened/closed by m-staged shift registers. As each switch SWb is opened/closed in sequence, a sampled signal is transferred to a video line as a time series signal and delivered to an external buffer BF.

Figure 6:
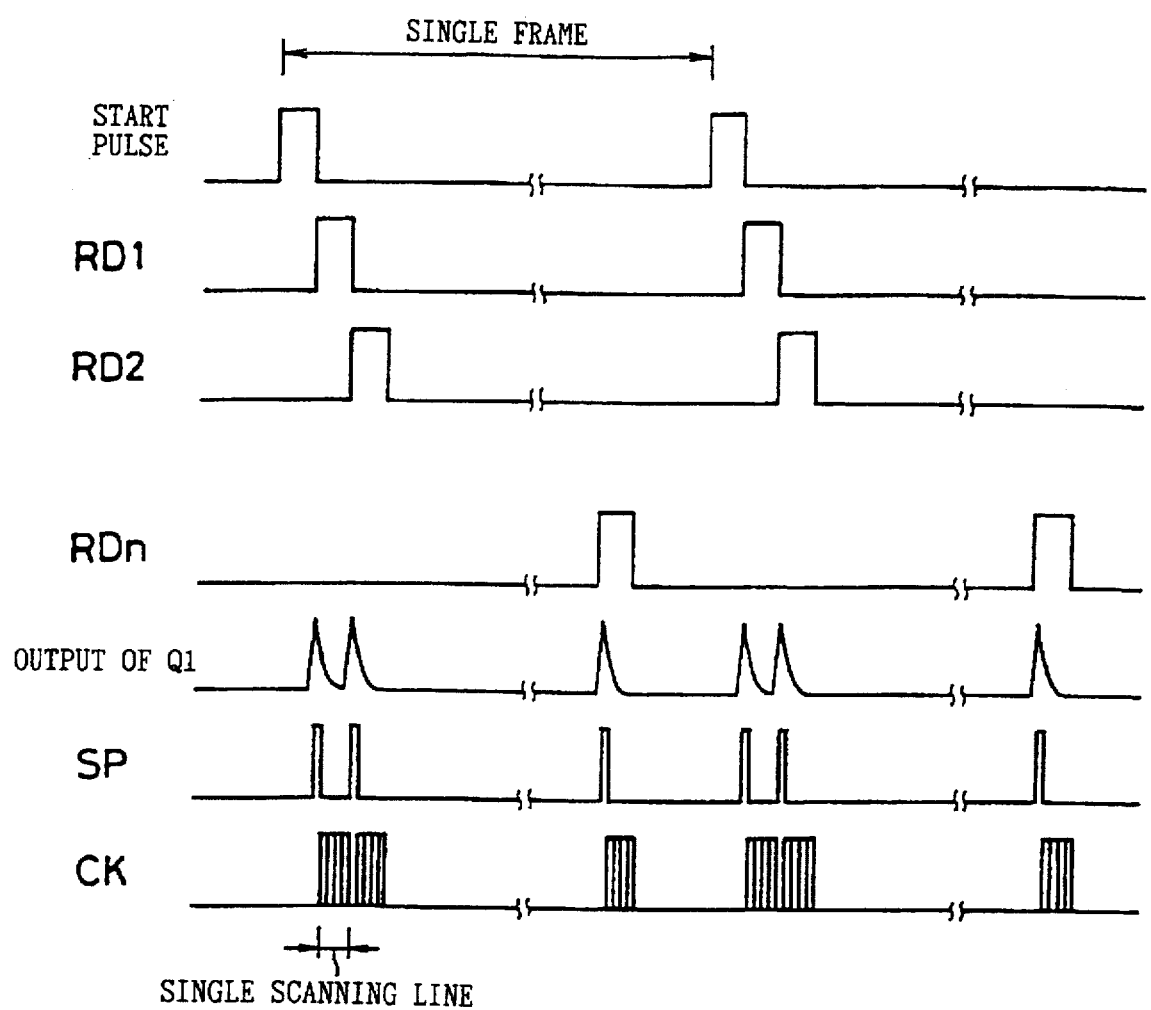
FIG. 6 is a timing chart showing the operation of the drive circuit shown in FIG. 5.

FIG. 6 is a timing chart showing the operation of the drive circuit shown in FIG. 5. The timing is explained as follows by taking an example where a shift register is used as the selection circuit SL. The address selection circuit SL is actuated by a start pulse from the CPU 21 and a first-column reading pulse RD1, a second-column reading pulse RD2, ..., and an nth-column reading pulse RDn in sequence.

When the first-column reading pulse RD1 is supplied to the gate of each switch SW at the first column, the amount of charges corresponding to the amount of incoming light entering each photodiode PD at the first column is read and a voltage signal is outputted from the operational amplifier Q1. Next, a sampling pulse SP is supplied to each sample-and-hold circuit so as to perform sampling at the peak of the output of the operational amplifier Q1. The sampled signals are supplied to the shift registers SR, and transferred by a shift clock CK composed of m pieces of pulses before the next sampling pulse SP is supplied, and then outputted externally as an image signal for a single scanning line. The same operation is performed in the second and following columns. That is to say, signals for m rows are read in parallel by a single reading pulse, and a time series signal for a single scanning line is formed by the shift registers SR.

Figure 7:
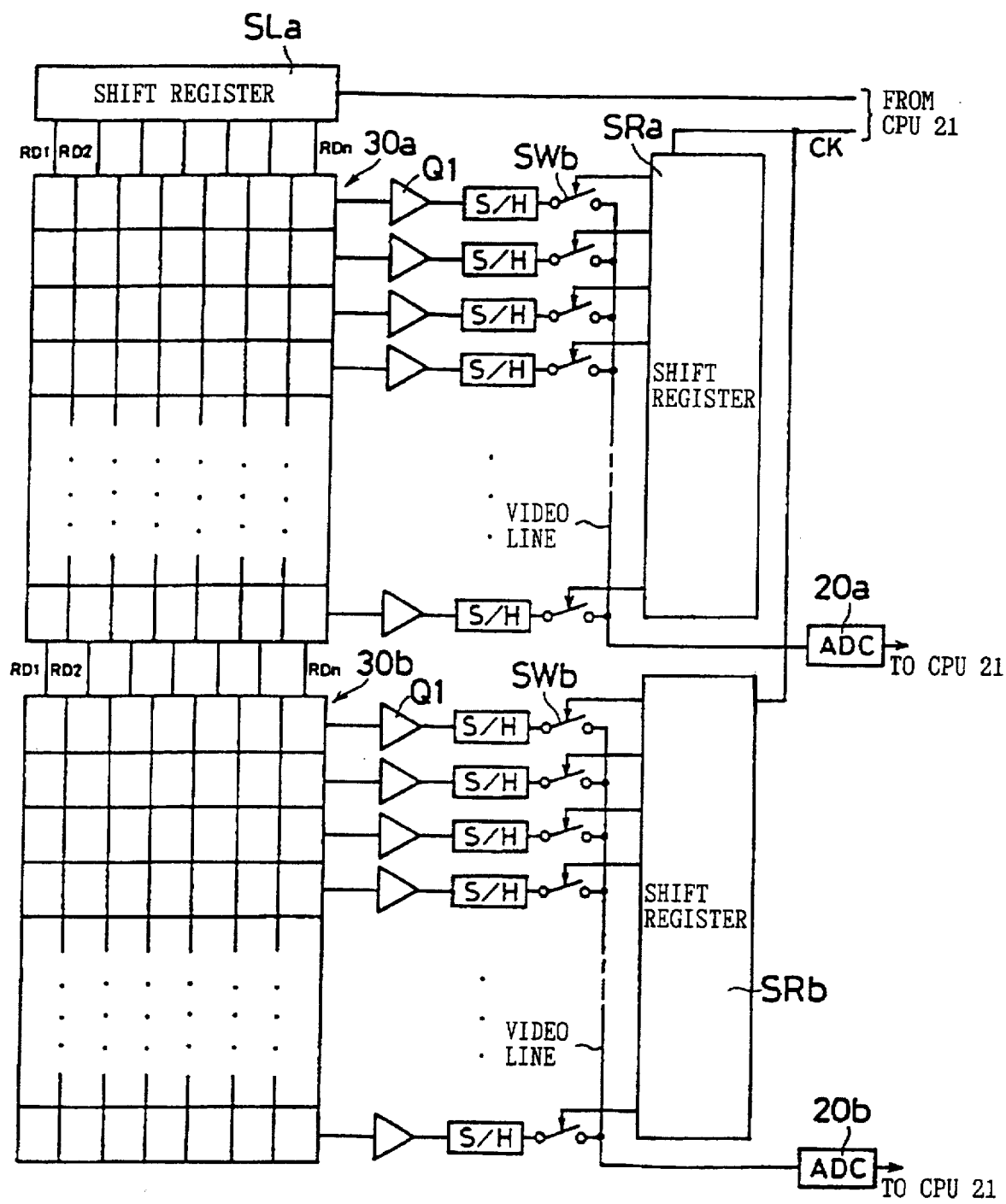
FIG. 7 is a circuit diagram wherein MOS image sensors are connected in multistages.

FIG. 7 shows an embodiment of a circuit where MOS image sensors are connected in multistages. Two MOS image sensors 30a, 30b, each having light-receiving pixels in a matrix of m rows X n columns, are arranged adjacent to each other in the direction of the row, and connected to each other so as to drive each column by using one of the reading pulses (RD1 to RDn corresponding to the column) outputted from the shift register SLa which is an address selection circuit SL. By a single reading pulse, signals are read in parallel from 2 m pieces of photodiodes and supplied to 2 m pieces of operational amplifiers Q1 and 2 m pieces of sample-and-hold circuits corresponding to each row. Two shift registers SRa, SRb are arranged to correspond to the two MOS image sensors 30a, 30b, respectively. The outputs from the sample-and-hold circuits are transferred to the video lines as time series signals by sequentially opening/closing 2 m pieces of switches SWb. The output signals on the video lines are supplied to two AD converters 20a, 20b, respectively, converted into digital data and supplied to the CPU 21. In this way, the imaging region of the apparatus can be extended, and data can be transferred quickly as a whole. Although two MOS image sensors connected in multistages are explained above, three or more MOS image sensors may also be used.

Figure 8:
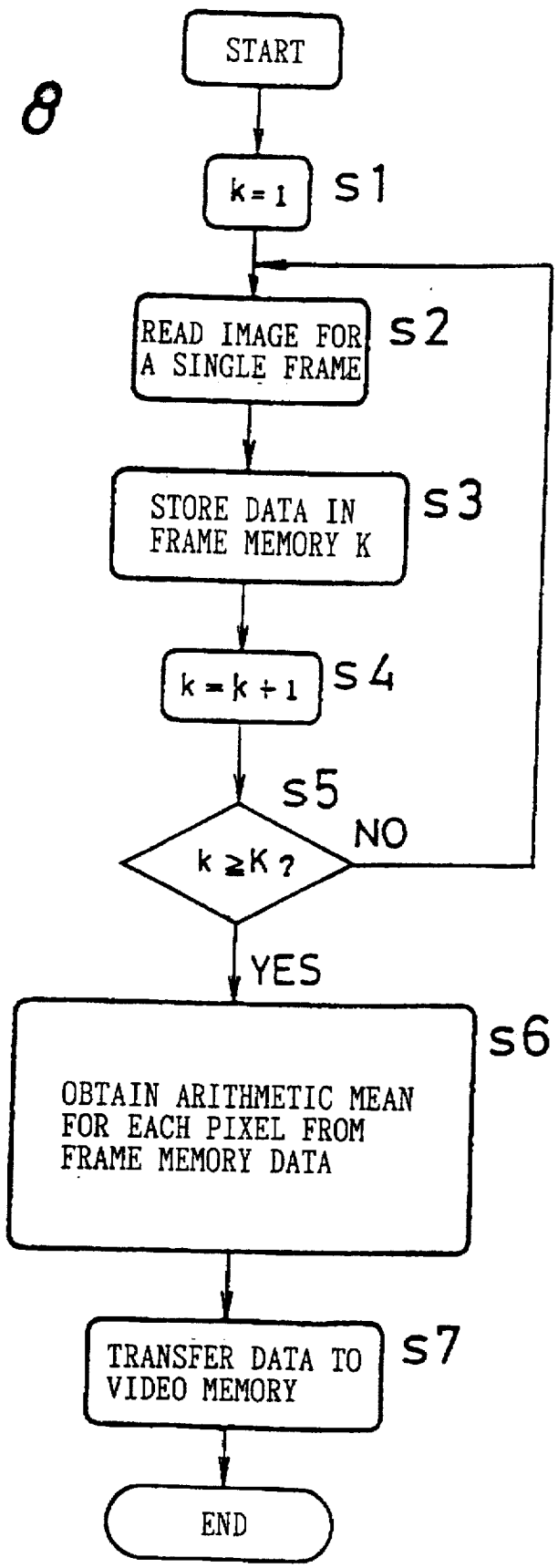
FIG. 8 is a flowchart showing a linear tomographic imaging procedure.
Figure 9:
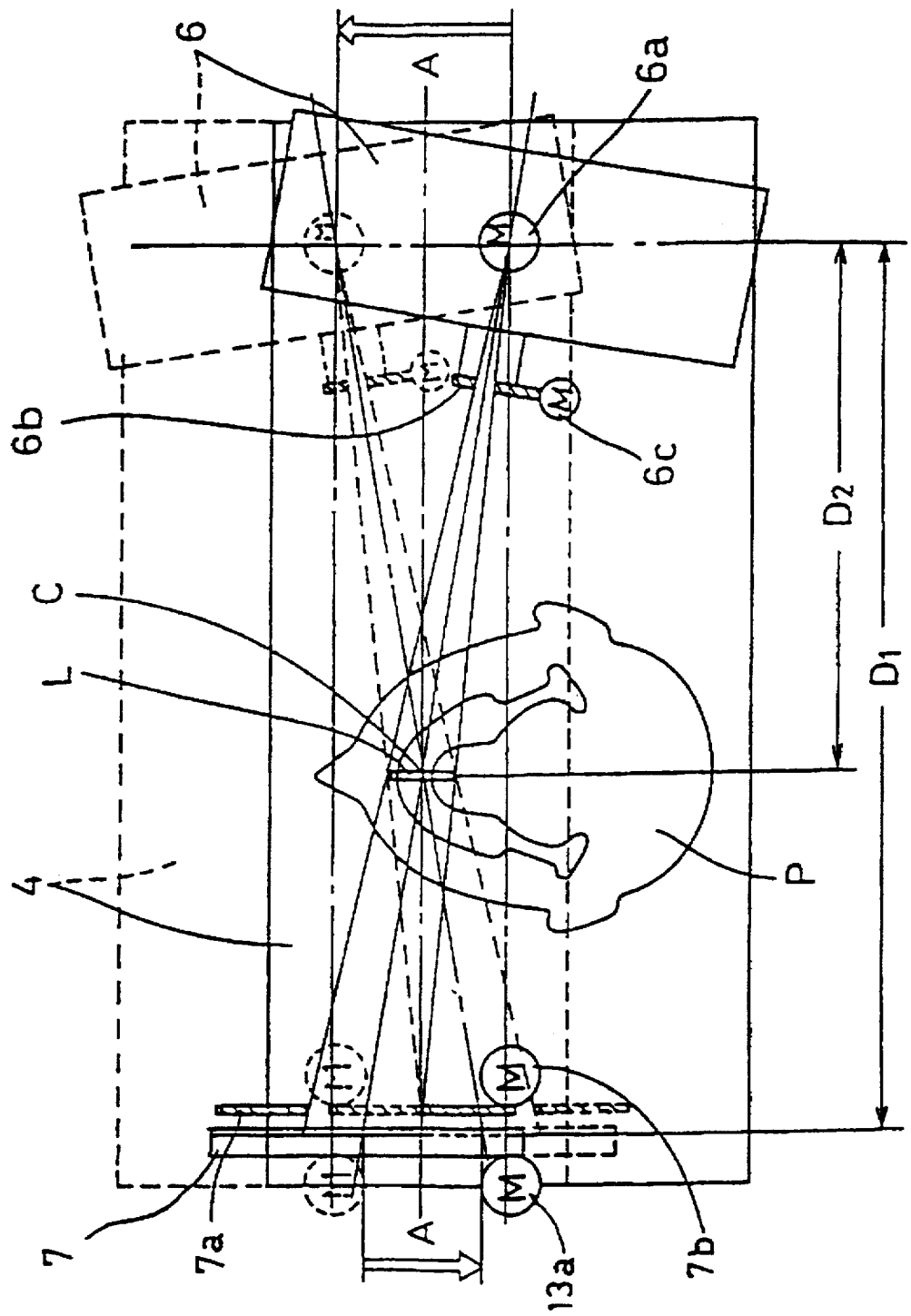
FIG. 9 is an explanatory view showing linear tomographic imaging.

FIG. 8 is a flowchart showing a linear tomographic imaging procedure, and FIG. 9 is an explanatory view showing linear tomographic imaging. First, the operation principle of linear tomographic imaging is described below. As shown in FIG. 1, a patient P, namely a subject, sits on the chair 8, and the head of the patient P is secured with positioning members 5. The horizontal movement mechanism 3 is then controlled so as to align the longitudinal direction of the swivel member 4 with the center line A—A shown in FIG. 9. While the X-ray imaging device 7 is moved downward in the drawing, the X-ray source 6 is moved upward in the drawing. In accordance with this movement, the X-ray source 6 is rotated so that the center of the X-ray beams emitted from the X-ray source 6 passes the center C of a horizontal tomographic plane L and enter the same position of the X-ray imaging device 7 at all times.

At this time, in the imaging region of the X-ray imaging device 7, the image of the same portion of the horizontal tomographic plane L enters the same position at all times. However, the images at the portions other than the horizontal tomographic plane L slide and are blurred. As a result, only the portion of the horizontal tomographic plane L is imaged clearly. A second slit plate 7a shown in FIG. 9 is driven by a motor 7b, and the X-ray imaging device 7 is moved by a motor 13a constituting the slide mechanism 13.

In the above-mentioned explanation, the X-ray source 6 and the X-ray imaging device 7 are moved linearly with respect to the center C of the horizontal tomographic plane L. However, a similar linear tomographic image can also be obtained by rotating the X-ray source 6 and the X-ray imaging device 7 around the center C.

When linear tomographic imaging is performed by using the digital X-ray imaging apparatus of the invention, the X-ray source 6 and the X-ray imaging device 7 are moved at a constant speed and an X-ray image of the subject is taken by the MOS image sensor each time a predetermined amount of movement takes place so as to obtain images at intervals of a small displacement of the imaging angle. After the image data is obtained and stored in a plurality of frame memories 22, tomographic images are reproduced by arithmetic processing.

Referring to FIG. 8, parameter k is initialized to 1 in step s1. In step s2, imaging is started, and the image data for a single frame is read when the X-ray source 6 and the X-ray imaging device 7 are at their predetermined positions. In step s3, the data is stored in kth frame memory. Next, the parameter k is incremented by one. In step s5, whether the kth imaging operation is completed or not is determined. In this way, the procedure of steps s2 to s5 are repeated. Consequently, K pieces of image data taken at intervals of a small displacement of the imaging angle are stored in the frame memories 22.

After imaging is completed, the image data stored in each frame memory is calculated in step s6 so as to obtain an arithmetic mean for each pixel. In this way, the image of the horizontal tomographic plane L is made clear by the addition. The portions other than the horizontal tomographic plane L are buried in the background. Next, in step s7, the reproduced tomographic image data is transferred to the video memory 24 and displayed by the image display unit 26.

Figure 10:
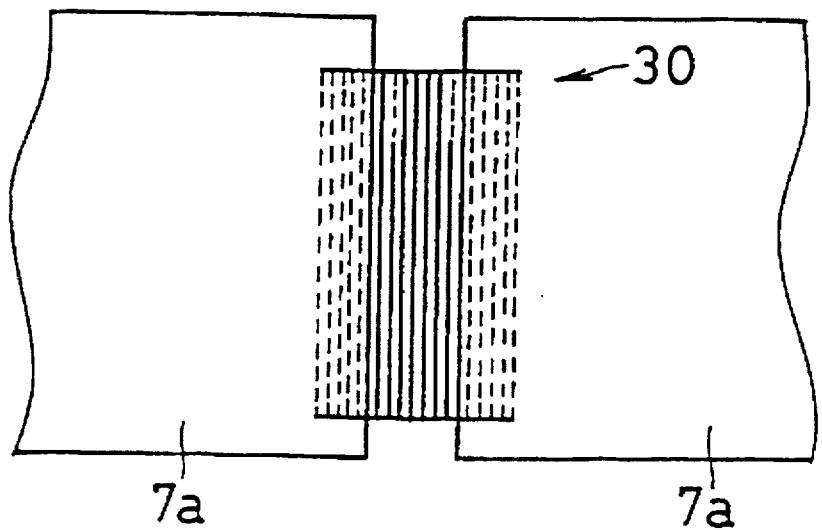
FIG. 10 is an explanatory view showing panoramic tomographic imaging.
Figure 11:
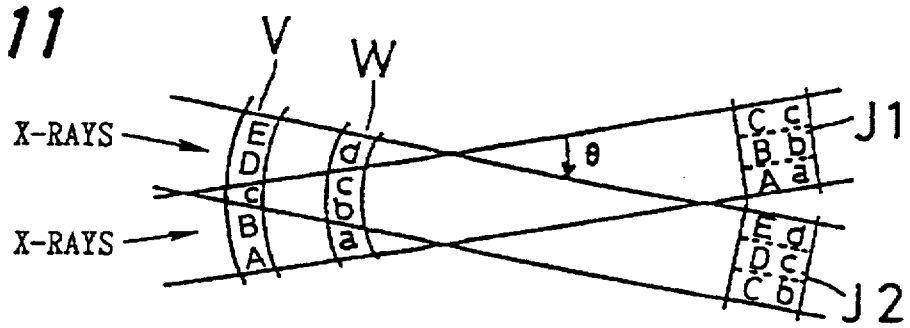
FIG. 11 is an explanatory view showing panoramic tomographic imaging.
Figures 12, 13:
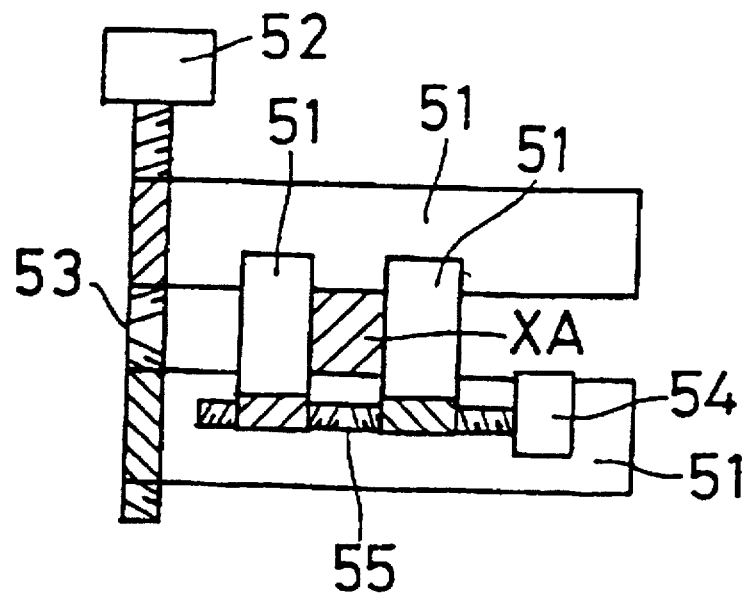

FIGS. 10 to 12 are explanatory views showing panoramic tomographic imaging. Referring to FIG. 10, the opening of the second slit plate 7a is narrowed, and the imaging region of the MOS image sensor 30 is partially limited to approximately 6 mm wide×150 mm long, for example. Furthermore, the reading pixel range of the MOS image sensor is selectively changed by the address selection circuit SL shown in FIG. 5. Moreover, with the second slit plate 7a kept open widely for linear imaging and uncontrolled, only the light-receiving region of the MOS image sensor 30 can be controlled for both panoramic and linear imaging as a matter of course.

When the digital X-ray imaging apparatus of the invention is used for panoramic tomographic imaging, the swivel member 4 rotates around the subject with the X-ray source 6 and the X-ray imaging device 7 opposingly each other, and X-ray images of the subject are taken by the MOS image sensor 30 at intervals of a predetermine rotation angle. After the image data taken at intervals of a small displacement of the imaging angle is stored in a plurality of frame memories 22, tomographic images are reproduced by arithmetic operation processing.

Referring to FIG. 11, objects A, B, C, D and E are arranged on a tomographic plane V, and objects a, b, c and d are arranged on a tomographic plane W. Image information J1 at a certain imaging angle is obtained as the overlap of the images of the objects A and a, the overlap of the images of the objects B and b, and the overlap of the images of the objects C and c. When the imaging angle is changed by angle θ, image information j2 is obtained as the overlap of the images of the objects C and b, the overlap of the images of the objects D and c, and the overlap of the images of the objects E and d.

In FIG. 12a, the image information J1 and the image information J2 thus obtained are added directly. The object images on the tomographic plane V and having the same level are added to the object images on the tomographic plane W and having the same level on a unit-by-unit basis. In FIG. 12b, the contents of the image information J1 are shifted by one step to create shift image information J1s. In FIG. 12c, the shift image information J1s is added to the image information J2. As a result, each of the images of the objects b, c and d has two units in each stage, and each of the images of the objects B, C, D and E remains as one unit. Therefore, by repeating this kind of shift processing and addition processing many times, the images of the objects a, b, c and d on the desired tomographic plane W are added one after another, and the images of the objects other than those on the tomographic plane W are buried in the background. Consequently, the panoramic tomographic images along the desired tomographic plane can be reproduced.

Figure 14:
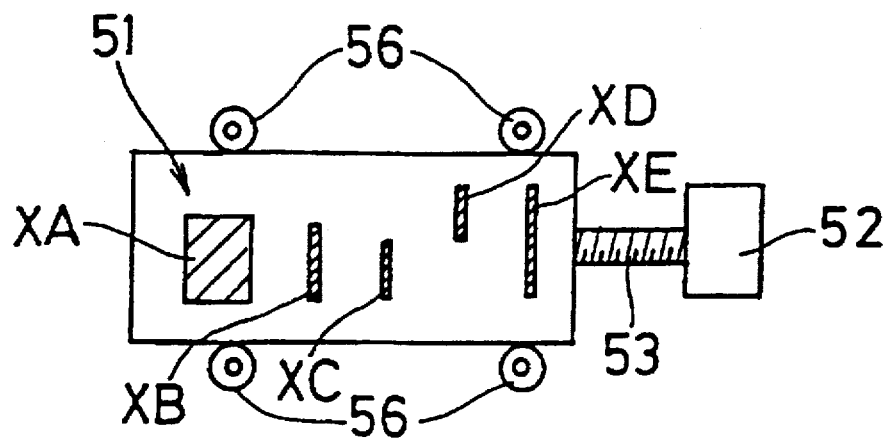
Figure 15:
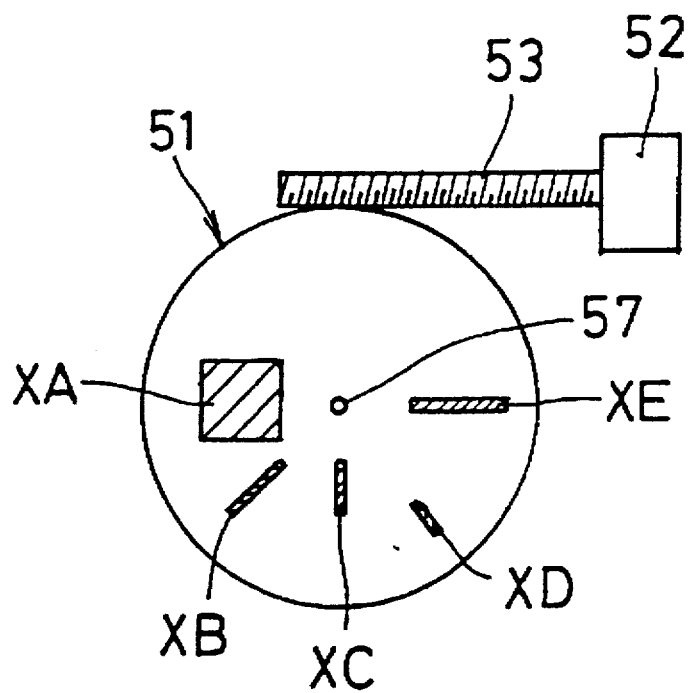

FIGS. 13 to 15 are structural views showing embodiments of the first slit plate 6b and the second slit plate 7a. In FIG. 13, a pair of X-ray shielding plates 51 are threadedly engaged with a screw 53 having two opposite-direction male threads. When the screw 53 is rotated by a motor 52, the opening width of the X-ray shielding plate 51 in the vertical direction is adjusted. In the same way, a screw 55 having two opposite-direction male threads is disposed perpendicularly to the screw 53 and threadedly engaged with the pair of the X-ray shielding plates 51. When the screw 55 is rotated by a motor 54, the opening width of the X-ray shielding plate 51 in the horizontal direction is adjusted. Consequently, the dimension of an opening XA can be adjusted as desired.

In FIG. 14, a rectangular X-ray shielding plate 51 is supported by rolls 56 and mounted on a screw 53. When the screw 53 is rotated by a motor 52, the X-ray shielding plate 51 is moved linearly in the horizontal direction. The X-ray shielding plate 51 is provided with a plurality of openings XA to XE having different dimensions, and these openings can be selectively used in accordance with the movement position.

In FIG. 15, a disc-shaped X-ray shielding plate 51 is supported by a shaft 57, and a threaded portion formed around the circumference of the shielding plate 51 is threadedly engaged with a worm screw 53. When the screw 53 is rotated by a motor 52, the X-ray shielding plate 51 is rotated. The X-ray shielding plate 51 is provided with a plurality of openings XA to XE having different dimensions, and these openings can be selectively used in accordance with the rotation position.

As described above, the opening ranges of the first slit plate 6b and the second slit plate 7a can be changed easily depending on imaging conditions.

Figure 16:
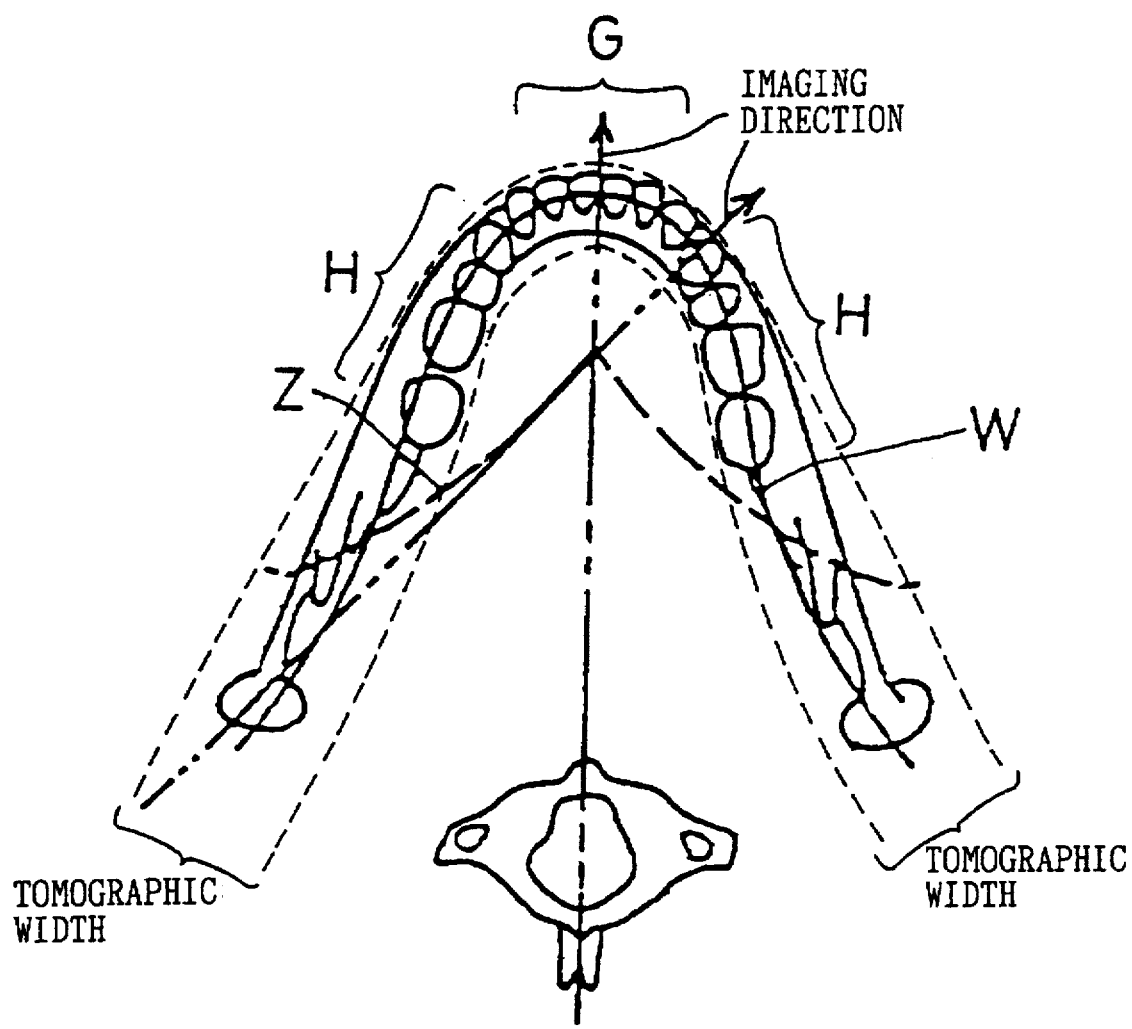
FIG. 16 is an explanatory view showing a rotation center orbit and a tomographic plane in the panoramic tomographic imaging mode.

FIG. 16 is an explanatory view showing a rotation center orbit and a tomographic plane in the panoramic tomographic imaging mode. The swivel member 4 moves so that X-rays from the X-ray source 6 can enter the tomographic plane W nearly perpendicularly, and the distance from the rotation center to the tomographic plane, that is, the effective rotation radius, changes depending on the curvature radius of the tomographic plane W to be imaged. Consequently, the rotation center of the swivel member 4 moves along an orbit Z represented by a smooth curve having a bent portion in the middle.

When the front tooth region G is to be imaged, the effective rotation radius becomes small. Therefore, there is a fear that the tomographic width in the front tooth region G corresponding to the reproduction range of a tomographic image may be smaller than the tomographic width in the molar tooth region H. To solve this problem, the range of the reading pixels of the MOS sensor is narrowed by adjustment, whereby the tomographic width in the front tooth region G is made larger. This is effective in easily positioning the patient. Consequently, the width of the tomographic image can be adjusted by controlling at least the range of the reading pixels of the MOS sensor. However, the width of the tomographic image can also be adjusted by controlling the range of the reading pixels of the MOS sensor and/or the opening width of the second slit plate 7a during X-ray imaging.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A digital X-ray imaging apparatus comprising:

an X-ray generator for emitting X-rays toward a subject:

an X-ray imaging device for detecting an image of X-rays having passed through the subject, said X-ray imaging device including a MOS sensor means having a plurality of light-receiving pixels arranged in two dimensions, said MOS sensor means further for selecting which of said plurality of light receiving pixels are read as an imaging signal;

means for moving the X-ray generator and the X-ray imaging device that are opposed to each other, relative to the subject;

means for signal processing to produce a tomographic image in accordance with said imaging signal from the X-ray imaging device; and means for displaying a tomographic image produced by the signal processing means.

2. The digital X-ray imaging apparatus according to claim 1, wherein an X-ray imaging device further comprises a plurality of MOS sensors connected in multistages, a pixel selection circuit for selecting reading pixels for each MOS sensor and a plurality of shift registers for receiving an image signal from each light-receiving pixel disposed and selected for each MOS sensor and for transferring the image signal on the basis of time series.

3. The digital X-ray imaging apparatus according to claim 1 or 2, further comprising means for selecting a panoramic or linear tomographic imaging mode, wherein the ranges of pixels to be read by the MOS sensor is selected in accordance with the selected imaging mode.

4. The digital X-ray imaging apparatus according to claim 3, further comprising a first slit plate for limiting the X-ray irradiation field of the subject and a second slit plate for limiting the X-ray incoming region of the X-ray imaging device, wherein the opening ranges of the first and second slit plates are selectively changed in accordance with the selected panoramic or linear imaging mode.

5. The digital X-ray imaging apparatus according to claim 3, wherein the opening width of the second slit plate is adjusted during imaging in the panoramic tomographic imaging mode.

6. The digital X-ray imaging apparatus according to claim 4, wherein the opening width of the second slit plate is adjusted during imaging in the panoramic tomographic imaging mode.

* * * * *